US012685311B2

(12) United States Patent
Geissler et al.

(10) Patent No.: US 12,685,311 B2
(45) Date of Patent: Jul. 21, 2026

(54) ENVIRONMENTALLY FRIENDLY BIOCIDAL QUATERNIZED AMINE COMPOUND

(71) Applicant: Baker Hughes Oilfield Operations LLC, Houston, TX (US)

(72) Inventors: Brett L Geissler, Richmond, TX (US); Carlos M. Menendez, Houston, TX (US)

(73) Assignee: Baker Hughes Oilfield Operations LLC, Houston, TX (US)

( * ) Notice: Subject to any disclaimer, the term of this patent is extended or adjusted under 35 U.S.C. 154(b) by 338 days.

(21) Appl. No.: 18/369,177

(22) Filed: Sep. 17, 2023

(65) Prior Publication Data

US 2025/0089711 A1 Mar. 20, 2025

(51) Int. Cl.

| | |
|---|---|
| ***C07C 229/12*** | (2006.01) |
| ***A01N 33/12*** | (2006.01) |
| ***A01N 37/34*** | (2006.01) |
| ***A01N 37/44*** | (2006.01) |
| ***A01N 59/26*** | (2006.01) |
| ***C02F 1/50*** | (2023.01) |
| ***C07C 227/02*** | (2006.01) |
| ***C09K 8/60*** | (2006.01) |
| *C02F 103/10* | (2006.01) |
| *C02F 103/36* | (2006.01) |

(52) U.S. Cl.

CPC ............. *A01N 37/44* (2013.01); *A01N 33/12* (2013.01); *A01N 37/34* (2013.01); *A01N 59/26* (2013.01); *C02F 1/50* (2013.01); *C07C 227/02* (2013.01); *C07C 229/12* (2013.01); *C09K 8/605* (2013.01); *C02F 2103/10* (2013.01); *C02F 2103/365* (2013.01)

(58) Field of Classification Search

CPC ............................ C07C 227/02; C07C 229/12

See application file for complete search history.

(56) References Cited

U.S. PATENT DOCUMENTS

| | | | |
|---|---|---|---|
| 7,951,754 | B2 | 5/2011 | Tiwari et al. |
| 9,445,598 | B2 | 9/2016 | Figueredo |
| 10,098,346 | B2 | 10/2018 | Geissler et al. |
| 2018/0163020 | A1 | 6/2018 | Zong et al. |
| 2021/0253938 | A1 | 8/2021 | Meng et al. |
| 2021/0378244 | A1 | 12/2021 | Vitomir |

FOREIGN PATENT DOCUMENTS

| | | | |
|---|---|---|---|
| CN | 110934144 | A | 3/2020 |
| EP | 3378313 | A1 | 9/2018 |
| WO | 2021019470 | A1 | 2/2021 |

OTHER PUBLICATIONS

Akram, M. et al., "An insight view on synthetic protocol, surface activity, and biological aspects of novel biocompatible quaternary ammonium cationic gemini surfactants", Journal of surfactants and detergents, 2021, vol. 24, pp. 35-49 abstract; scheme 1.

Guo, S. et al., "Antibacterial activities of five cationic gemini surfactants with ethylene glycol bisacetyl spacers", Journal of surfactants and detergents, 2014, vol. 17, pp. 1089-1097 pp. 1090, 1091, 1096; scheme 1.

Tawfik, S. M. et al., "Surface, thermodynamic and biological activities of some synthesized gemini quaternary ammonium salts based on polyethylene glycol", Journal of industrial and engineering chemistry, 2015, vol. 30, pp. 112-119 abstract; pp. 113, 118.

International Search Report and Written Opinion dated Dec. 26, 2024 for PCT/US2024/047078.

Haruna, H. , et al., "Gelatin: A green corrosion inhibitor for carbon steel in oil well acidizing environment", Journal of Molecular Liquids; 264; May 2018; 515-525.

*Primary Examiner* — Shawquia Jackson

(74) *Attorney, Agent, or Firm* — Crowe & Dunlevy, P.C.

(57) ABSTRACT

An environmentally friendly biocide is disclosed for managing microbe levels. The environmentally friendly biocide includes a quaternized amine of the structure:

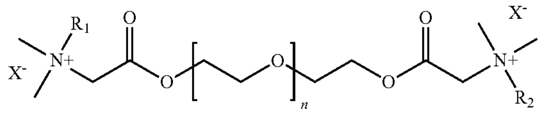

where X is chlorine, $R_1$ is a $C_{16}$-$C_{18}$ group, $R_2$ is a $C_{16}$-$C_{18}$ group, and n is within the range of 8 to 50. The environmentally friendly biocide optionally includes a solvent component. In one aspect, a method is disclosed for treating an oilfield system with an environmentally friendly biocide, where the method includes the steps of obtaining the environmentally friendly biocide and contacting the oilfield system with it. In yet another aspect, a method is disclosed for managing microbe levels in an oilfield system. The method involves obtaining an environmentally friendly biocide, introducing a first treatment of the environmentally friendly biocide into the oilfield system, and introducing a second treatment of the environmentally friendly biocide into the oilfield system.

20 Claims, No Drawings

ENVIRONMENTALLY FRIENDLY BIOCIDAL QUATERNIZED AMINE COMPOUND

FIELD OF THE INVENTION

The present application is generally directed at chemical formulations, and in particular to environmentally friendly biocides and method for using such biocides.

BACKGROUND OF THE INVENTION

Microbial proliferation can threaten the operation of oilfield equipment and fluids by introducing challenges such as corrosion failure. Souring and plugging from microbes can slow production rates and compromise the integrity of production equipment. Further, microbes may present serious health and safety risks to onsite workers.

To combat these issues, various biocides are used for microbial management. Although widely adopted, the use of certain biocides may pose severe environmental consequences. Fluids treated with biocides often contain residual biocide moieties, and because most biocides are broadly toxic to all life, any organisms that subsequently encounter the treated fluids may be harmed. Very few environmentally friendly biocidal active compounds are presently available.

A need therefore exists for environmentally friendly biocidal compounds to manage microbe levels while reducing the risks for the disposal of treated fluids and accidental environmental release. The present disclosure is directed at these and other deficiencies in the prior art.

SUMMARY OF THE INVENTION

In some embodiments, an environmentally friendly biocide is disclosed, where the environmentally friendly biocide includes a quaternized amine and a solvent. The quaternized amine has the structure:

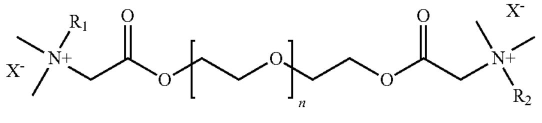

where X is chlorine, $R_1$ is a $C_{16}$-$C_{18}$ group, $R_2$ is a $C_{16}$-$C_{18}$ group, and n is within the range of 8 to 50.

In other embodiments, a method of treating an oilfield system with an environmentally friendly biocide is disclosed, where the method involves obtaining the environmentally friendly biocide and contacting the oilfield system with it. The environmentally friendly biocide includes a quaternized amine of the structure:

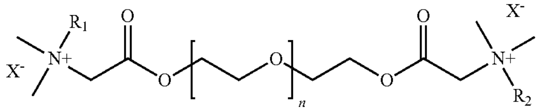

where X is chlorine, $R_1$ is a $C_{16}$-$C_{18}$ group, $R_2$ is a $C_{16}$-$C_{18}$ group, and n is within the range of 8 to 50.

In yet other embodiments, a method of managing microbe levels in an oilfield system is disclosed, where the method includes the steps of obtaining an environmentally friendly biocide, introducing a first treatment of the environmentally friendly biocide into the oilfield system, and introducing a second treatment of the environmentally friendly biocide into the oilfield system. The environmentally friendly biocide includes a quaternized amine of the structure:

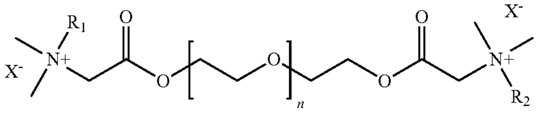

where X is chlorine, $R_1$ is a $C_{16}$-$C_{18}$ group, $R_2$ is a $C_{16}$-$C_{18}$ group, and n is within the range of 8 to 50.

DETAILED DESCRIPTION

The present disclosure focuses on the formulation and use of novel biocides to reduce microbe levels in oilfield systems. It has been discovered that an environmentally friendly biocide with a quaternized amine can be used to treat microbial growth in an oilfield system while avoiding the introduction of downstream environmental and health hazards. The quaternized amine component of the environmentally friendly biocide has a propensity to biodegrade quickly and completely and does not accumulate within various organisms, i.e., it is not a persistent, bio-accumulative and toxic (PBT) or very persistent and very bio-accumulative (vPvB) substance or mixture. Based on the foregoing, the quaternized amine is not expected to cause adverse environmental effects related to ozone depletion, photochemical ozone creation potential, endocrine disruption, or global warning potential.

The quaternized amine is a diester diquat, which can be obtained by reacting a polyalkylene glycol, chloroacetic acid, and a tertiary fatty amine. In one embodiment, the quaternized amine is di(dimethyl(alkyl)ammonium chloride) ethanoyloxy-oxo, which has a structure of:

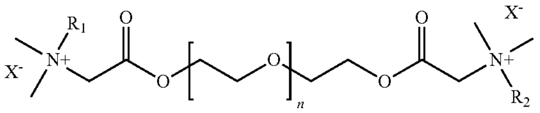

where X is chlorine (Cl), and each R group ($R_1$ and $R_2$) is independently a $C_{16}$-$C_{18}$ group. In one embodiment, n is within the range of 8 to 50. Alternatively, n is within the range of 9 to 15; this range may be obtained, for example, in embodiments where the polyalkylene glycol is PEG 600. In yet another embodiment, n is within the range of 30 to 40; PEG 1500 may be used as the polyalkylene glycol to obtain this range for n of the polymer.

In one embodiment, the environmentally friendly biocide further includes a solvent. Suitable solvents include isopropanol, ethanol, propylene carbonate, methanol, and polyethylene glycol.

In one embodiment where the environmentally friendly biocide includes a solvent component, the quaternized amine and the solvent are present in a ratio of between about 1:10 to about 8:1 (quaternized amine:solvent). In another embodiment, the quaternized amine and the solvent are present in a ratio of about 1:1. As used herein, ranges of concentration ratios should be interpreted to include any and all ratios within the prescribed ranges. For example, embodiments where the ratio of quaternized amine to solvent is expressed within the range of about 1:10 to about 8:1 should be interpreted to also include the discrete intermediate concentrations ratios of 1:9, 1:8, 1:7 . . . 5:1, 6:1, 7:1 (quaternized amine:solvent), and fractional ratios therebetween (e.g., 1:9.9, 1:9.8, 7.5:1, and 7.7:1).

In one embodiment, the environmentally friendly biocide also includes an aldehyde. The aldehyde component of the environmentally friendly biocide may impart additional biocidal properties to the environmentally friendly biocide. By way of non-limiting example, the aldehyde in various embodiments may be glutaraldehyde, formaldehyde, cinnamaldehyde, ortho-phthalaldehyde, acraldehyde, or glyoxal.

The environmentally friendly biocide may additionally include at least one biocidal agent, which may impart further biocidal properties. Suitable biocidal agents for the environmentally friendly biocide include tetrakis(hydroxymethyl) phosphonium sulfate (THPS), 2,2-dibromo-3-nitrilopropionaminde (DBNPA), and didecyldimethylammonium chloride.

The success of treatments with the environmentally friendly biocide involves a reduction in microbial count. The environmentally friendly biocide is effective at managing microbes including but not limited to sulfate-reducing bacteria, acid-producing bacteria, and slime-producing bacteria. In various embodiments, the environmentally friendly biocide reduces the level of microbes by at least 70%, in another embodiment by at least 75%, in yet another embodiment by at least 80%, and in yet another embodiment by at least 85%. By way of non-limiting example, the environmentally friendly biocide of other embodiments reduces the level of microbes by between about 90% to 100%. It will be understood that, as used herein, a range of X % to Y % will be interpreted to include the disclosure of each discrete integer value between X and Y (e.g., X, X+1, X+2 . . . Y−1, Y). The environmentally friendly biocide may therefore reduce the level of microbes at values including but not limited to 95%, 96%, 97%, 98% and 99%.

In one embodiment, a method of using the environmentally friendly biocide involves contacting an oilfield system with a treatment of the environmentally friendly biocide. It will be appreciated that, in various non-limiting embodiments, the oilfield system may be an auxiliary water system, a wastewater system, an oilfield water flood or saltwater disposal system, or a fracturing fluid. Suitable oilfield systems may further include raw water sources, separators, ballasts, storage and mixing tanks, screens, surface injection equipment, production equipment such as injection and production piping and casing, completion and valving, downhole equipment, and well formations.

In one embodiment, the environmentally friendly biocide is added on a continuous basis to the oilfield system at a point of uniform mixing. Introduction of the environmentally friendly biocide at a point of uniform mixing allows the environmentally friendly biocide to disperse rapidly and uniformly to the desired area of treatment. The point of uniform mixing will vary depending on the equipment and the location of fouling. In an embodiment where the oilfield system is a water handling system, e.g., for oilfield injection or wastewater, the point of uniform mixing may be the holding tank. In another embodiment, where the oilfield system is a fracturing fluid, the point of uniform mixing may be a frac storage tank or a wellhead injection pipeline during the pumping of water downhole. The point of uniform mixing for a drilling, completion and workover fluids system may be a circulating, holding or mud tank. For packer fluids, the point of uniform mixing could be a circulating holding tank or another mixing device location. In yet another non-limiting exemplary embodiment, the point of uniform mixing for a wastewater system or sludge may be at a digester.

The frequency and effective amount of the treatment of environmentally friendly biocide will vary depending on the oilfield system to be treated and on the severity of the microbial contamination therein. Depending on the degree of fouling, the environmentally friendly biocide is added to the oilfield system by slug, on a continuous basis, or on an intermittent basis.

For continuous use, the effective amount of the environmentally friendly biocide to control slime-forming and sulfate-reducing bacteria is within the range of about 5 ppm to about 200 ppm. For example, in oilfield systems including but not limited to an oilfield water flood system or a saltwater disposal system, the effective amount for continuous use is between about 5 ppm to about 15 ppm active. In other embodiments, where the oilfield system is a wastewater or a point of oilfield injection, about 30 ppm of the environmentally friendly biocide is added continuously to the system while the system is noticeably fouled, followed by continuous treatments at about 15 ppm to maintain control once fouling becomes initially reduced. The environmentally friendly biocide in another embodiment is added to a wastewater system or sludge continuously in an amount from about 5 ppm to about 180 ppm.

For treatment by slug or by intermittent application, the effective amount of environmentally friendly biocide is within the range of about 5 ppm to about 1,000 ppm in the oilfield system. For oilfield systems such as an oilfield water flood system, a saltwater disposal system, a fracturing fluid, and a flowback return water (e.g., from post hydraulic fracturing), the effective amount for slug treatment is between about 5 ppm to about 60 ppm active. For intermittent treatment in these same oilfield systems, between about 5 ppm to about 400 ppm active is injected for four to eight hours per day, one to four times a week as needed to maintain microbial control. Where the oilfield system is a noticeably fouled wastewater or a point of oilfield injection, an intermittent treatment of about 180 ppm can be added over a period of four to six hours one or more times per week; the treatment amount is subsequently reduced to about 90 ppm to maintain control once fouling becomes initially reduced. For oilfield systems in pipeline pigging and scraping operations, the environmentally friendly biocide is added to slug water immediately following the scraper at an effective concentration of between about 75 ppm to about 500 ppm active depending on the length of the pipeline and the severity of the biofouling. In gas production and transmission pipelines, intermittent injections (e.g., weekly, or as needed to maintain control) are made at an active concentration range of about 500 ppm to about 1,000 ppm. For individual injection wells, between about 65 ppm to about 1,000 ppm is added intermittently (e.g., yearly, or as needed to maintain control) before gas is injected. For drilling, completion, and workover fluids systems, between about 65 ppm to about 1000 ppm active is added to a freshly prepared fluid and, optionally, intermittently added for maintenance. For water used to hydrotest pipelines or vessels, between about 65 ppm to about 1,000 ppm active is injected depending on the water quality and length of time the equipment will remain idle.

EXAMPLE 1

Laboratory tests were performed to observe the environmentally friendly biocide of one embodiment for its ability to reduce microbial populations. The performance of the environmentally friendly biocide was further compared with that of two non-biodegradable biocidal quaternary amine compounds: alkyldimethylbenxylammonium chloride (ADBAC) and didecyldimethylammonium chloride (DDAC).

Test bottles were prepared with oilfield produced waters amended with nutrients containing a range of microbes. These bottles were treated with 400 ppm of either di(dimethyl(alkyl)ammonium chloride) ethanoyloxy-oxo, ADBAC, or DDAC, with one test bottle left as an untreated control. After four hours, ATP quantification and serial dilution using Modified Postgate's B media were performed for the various test bottles. The non-biodegradable compounds each reduced the microbial population via ATP by approximately 99% (with 99.16% reduction for ADBAC and 99.06% for DDAC). By comparison, the di(dimethyl (alkyl)ammonium chloride) ethanoyloxy-oxo reduced the microbial population by 96.79%. Similarly, serial dilution testing showed that all three treatments demonstrated a reduction in sulfate reducing microbes by 3-log units versus the untreated control sample. These results demonstrate that the environmentally friendly biocide performs comparably to nonbiodegradable biocides, while offering the additional advantage of reducing the risks of negative environmental impact.

In the foregoing specification, the invention has been described with reference to specific embodiments thereof. However, it will be evident that various modifications and changes can be made thereto without departing from the broader scope of the invention as set forth in the appended claims. Accordingly, the specification is to be regarded in an illustrative rather than a restrictive sense. For example, solvents, aldehydes, biocidal agents, treatment procedures, concentrations, proportions, dosages, and amounts not specifically identified or described in this disclosure or not evaluated in a particular Example are still expected to be within the scope of this invention.

The present invention may suitably comprise, consist of, or consist essentially of the elements disclosed and may be practiced in the absence of an element not disclosed. As used herein, the singular forms "a," "an," and "the" are intended to include the plural forms as well, unless the context clearly indicates otherwise. As used herein, the term "about" in reference to a given parameter is inclusive of the stated value and has the meaning dictated by the context (e.g., it includes the degree of error associated with measurement of the given parameter, i.e., ±5% of the stated value). As used herein, the term "and/or" includes any and all combinations of one or more of the associated listed items.

It is claimed:

1. An environmentally friendly biocide comprising:

a quaternized amine of the structure:

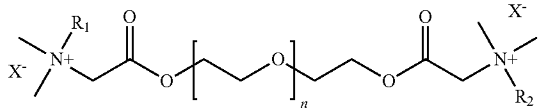

where X is chlorine, $R_1$ is a $C_{16}$-$C_{18}$ group, $R_2$ is a $C_{16}$-$C_{18}$ group, and n is within the range of 8 to 50;

a solvent; and an aldehyde selected from the group consisting of glutaraldehyde, formaldehyde, cinnamaldehyde, ortho-phthalaldehyde, acraldehyde, and glyoxal.

2. The environmentally friendly biocide of claim 1, wherein the solvent is selected from the group consisting of isopropanol, ethanol, propylene carbonate, methanol, and polyethylene glycol.

3. The environmentally friendly biocide of claim 1, wherein the quaternized amine and the solvent are present in a ratio of between about 1:10 to about 8:1 (quaternized amine:solvent).

4. The environmentally friendly biocide of claim 1, wherein the quaternized amine and the solvent are present in a ratio of about 1:1.

5. The environmentally friendly biocide of claim 1 further comprising:

at least one biocidal agent selected from the group consisting of 2,2-dibromo-3-nitrilopropionaminde, tetrakis (hydroxymethyl)phosphonium sulfate, and didecyldimethylammonium chloride.

6. A method of treating an oilfield system with an environmentally friendly biocide, the method comprising the steps of:

obtaining the environmentally friendly biocide, wherein the environmentally friendly biocide comprises a quaternized amine of the structure:

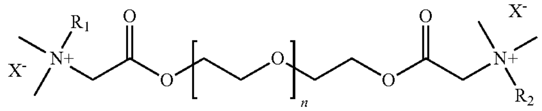

where X is chlorine, $R_1$ is a $C_{16}$-$C_{18}$ group, $R_2$ is a $C_{16}$-$C_{18}$ group, and n is within the range of 8 to 50; and contacting the oilfield system with the environmentally friendly biocide.

7. The method of claim 6, wherein the oilfield system is selected from an auxiliary water system, a wastewater system, an oilfield water flood system, a saltwater disposal system, and a fracturing fluid.

8. The method of claim 6, wherein the step of obtaining the environmentally friendly biocide further comprises the step of synthesizing the quaternized amine from a polyalkylene glycol, chloroacetic acid, and a tertiary fatty amine.

9. The method of claim 6, wherein the step of obtaining the environmentally friendly biocide further comprises the step of mixing the quaternized amine with an aldehyde selected from the group consisting of glutaraldehyde, formaldehyde, cinnamaldehyde, ortho-phthalaldehyde, acraldehyde, and glyoxal.

10. The method of claim 6, wherein the step of obtaining the environmentally friendly biocide further comprises the step of mixing the quaternized amine with a biocidal agent selected from the group consisting of tetrakis(hydroxymethyl)phosphonium sulfate, 2,2-dibromo-3-nitrilopropionaminde, and didecyldimethylammonium chloride.

11. The method of claim 6, wherein the step of contacting the environmentally friendly biocide with the oilfield system further comprises introducing an amount effective to reduce a microbe level in the oilfield system by at least 70%.

12. The method of claim 6, wherein the step of contacting the environmentally friendly biocide with the oilfield system further comprises introducing an effective amount of the environmentally friendly biocide at a point of uniform mixing.

13. The method of claim 6, wherein the step of contacting the environmentally friendly biocide with the oilfield system further comprises adding the environmentally friendly system to the system on a continuous basis.

14. The method of claim 6, wherein the step of contacting the environmentally friendly biocide with the oilfield system further comprises introducing an effective amount from about 5 ppm to about 1,000 ppm of the environmentally friendly biocide into the oilfield system.

15. A method of managing microbe levels in an oilfield system, the method comprising the steps of:

obtaining an environmentally friendly biocide, wherein the environmentally friendly biocide comprises a quaternized amine of the structure:

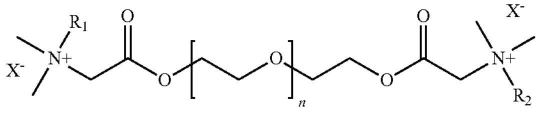

where X is chlorine, $R_1$ is a $C_{16}$-$C_{18}$ group, $R_2$ is a $C_{16}$-$C_{18}$ group, and n is within the range of 8 to 50;

introducing a first treatment of the environmentally friendly biocide into the oilfield system; and introducing a second treatment of the environmentally friendly biocide into the oilfield system.

16. The method of claim 15, wherein the step of obtaining the environmentally friendly biocide further comprises the step of mixing the quaternized amine with a solvent.

17. The method of claim 15, wherein the step of obtaining the environmentally friendly biocide further comprises the step of mixing the quaternized amine with an aldehyde selected from the group consisting of glutaraldehyde, formaldehyde, cinnamaldehyde, ortho-phthalaldehyde, acraldehyde, and glyoxal.

18. The method of claim 15, wherein the step of obtaining the environmentally friendly biocide further comprises the step of mixing the quaternized amine with a biocidal agent selected from the group consisting of tetrakis(hydroxymethyl)phosphonium sulfate, 2,2-dibromo-3-nitrilopropionaminde, and didecyldimethylammonium chloride.

19. The method of claim 15, wherein the first treatment comprises a higher concentration of the environmentally friendly biocide than the second treatment.

20. An environmentally friendly biocide comprising:

a quaternized amine of the structure:

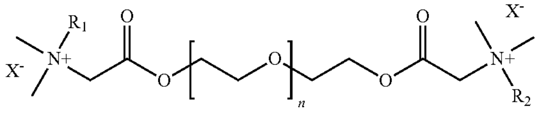

where X is chlorine, $R_1$ is a $C_{16}$-$C_{18}$ group, $R_2$ is a $C_{16}$-$C_{18}$ group, and n is within the range of 8 to 50;

a solvent; and at least one biocidal agent selected from the group consisting of 2,2-dibromo-3-nitrilopropionaminde, tetrakis (hydroxymethyl)phosphonium sulfate, and didecyldimethylammonium chloride.

* * * * *